United States Patent [19]

Gasco

[11] Patent Number: 5,250,236

[45] Date of Patent: Oct. 5, 1993

[54] METHOD FOR PRODUCING SOLID LIPID MICROSPHERES HAVING A NARROW SIZE DISTRIBUTION

[76] Inventor: Maria R. Gasco, Lungo Po Antonelli, 207 - 10153 Torino, Italy

[21] Appl. No.: 739,440

[22] Filed: Aug. 2, 1991

[51] Int. Cl.$^5$ .................... A61K 9/52; B01J 13/06
[52] U.S. Cl. .................... 264/4.4; 264/4.3; 424/498; 424/502; 427/213.3; 428/402.2; 428/402.24
[58] Field of Search ................ 264/4.3, 4.4; 427/213.3; 428/402.2, 402.24; 424/498, 502

[56] References Cited

U.S. PATENT DOCUMENTS

| | | | |
|---|---|---|---|
| 3,161,602 | 12/1964 | Herbig et al. | 264/4.4 |
| 3,804,776 | 4/1974 | Yazawa et al. | 264/4.4 |
| 3,856,699 | 12/1974 | Miyano et al. | 264/4.4 |
| 3,960,757 | 6/1976 | Morishita et al. | 427/213.3 |
| 4,331,654 | 5/1982 | Morris | 424/490 X |
| 4,776,991 | 10/1988 | Farmer et al. | 264/4.3 |
| 4,834,982 | 5/1989 | Putter | 424/458 |
| 4,880,634 | 11/1989 | Speiser | 424/502 X |
| 4,919,841 | 4/1990 | Kamel et al. | 427/213.3 X |
| 4,943,449 | 7/1990 | Aishima et al. | 427/213.3 |
| 5,004,756 | 4/1991 | Ogawa et al. | 514/655 |
| 5,039,527 | 8/1991 | Tabibi et al. | 424/450 |

FOREIGN PATENT DOCUMENTS

| | | |
|---|---|---|
| 0167825 | 1/1986 | European Pat. Off. |
| 0274431 | 7/1988 | European Pat. Off. |
| 3421468 | 12/1986 | Fed. Rep. of Germany |
| 61-249918 | 11/1986 | Japan |
| 61-263914 | 11/1986 | Japan |

OTHER PUBLICATIONS

"World Rev. Nutr. Diet", a. Shenking, 28, 37–46, 1978.
"Drugs Exptl. Res.", Y. Mizushima, XI (9), 595–600, 1985.
J. Pharm. Pharmacol., Y. Mizushima et al., 38, 132, 1986.
Arzneim-Forsch, Y. Ozawa et al., 36, (I), 689–690.
Pharm. Res., H. Yoshikawa et al., 5, 249, 1985.
Int. J. Pharm. R. Yoshikawa et al., 13, 321, 1983.
Pharm. Technol., J. Stanislaw et al., 33, (3), 154, 1987.

*Primary Examiner*—Richard D. Lovering
*Attorney, Agent, or Firm*—Oliff & Berridge

[57] ABSTRACT

Solid lipid microspheres having a diameter lower than one micron and a polydispersion of between 0.06 and 0.90 obtained by adding to a molten lipid substance a mixture consisting of water, a surfactant and possibly a co-surfactant, dispersing in water the obtained microemulsion, washing with water the dispersion microspheres by diafiltration and lyophilizing.

8 Claims, No Drawings

METHOD FOR PRODUCING SOLID LIPID MICROSPHERES HAVING A NARROW SIZE DISTRIBUTION

PRIOR ART

Lipid microspheres consisting of oil drops in an aqueous dispersion were first investigated for parenteral nutrition and more recently also as vehicles of pharmaceutical substances (Shenking A. World Rev. Nutr. Diet. 28, 1-111, 1978).

More recently systems based on soy oil emulsions, lecithin and suitable drug concentrations in water were developed for parenteral and oral administration (Mizushima Y. Drugs Exptl. Res., XI (9), 595-600, 1985; Mizushima Y. et al., J. Pharm. Pharmacol., 38, 132, 1986; Ozona Y. et al., Arzneim.-Forsch. 36, (I), 689-690; patents JP 61,249,918, Nov. 7, 1986 and JP 61,263,914, Nov. 21, 1986). Said systems do not have a well defined dimensional distribution of the oil drops nor stability with time.

Liquid emulsions were employed also by Hashida et al. for the lymphatic absorption of drugs (J. Pharmacokin. Biopharm. 3, 241-255, 1977). The prepared systems were particularly unstable and it was necessary to administer them within a very short time from the preparation.

Other liquid lipid system were prepared for oral administration and lymphatic absorption of drugs, such as linoleic acid and surface active agent mixtures (Josphikawa H. et al. Pharm. Res. 5, 249 (1985) or of bile salts and glycerylmonooleate (Joshikawa R. et al. Int. J. Pharm. 13, 321 (1983) 9.

Finally, microemulsions of oils in water should be mentioned, such as for instance those based on particles microemulsified and encapsulated in a coacervation film using substances such as phospholipids, polymerizable lecithins, sphingomyelins (EP 274431). Solid lipid microspheres were, on the other hands, suggested by Stanislw (Stanislaw J. Zdislaw J. Acta Pharm. Technol. 33 (3), 154, 1987). Such microspheres were prepared by mixing the active component with low melting materials, such as cetyl alcohol, polyoxyethylene glycol, stearic acid and white wax and forcing the melt through an orifice. The dimensions of the obtained microspheres were particularly coarse, with an average diameter larger than a micron.

Speiser also prepared lipid microparticles (DE 3421468). In this case the preparation was based on admixing the molten lipid with a surfactant by stirring at high speed and successive ultrasound treatment.

However, no close or uniform dimensional distribution could be obtained through said process.

SUMMARY

We have unexpectedly found that solid lipid microspheres of controlled dimensions and narrow dimensional distribution can be obtained through the process of the present invention which is characterized by:

a) contacting a molten lipid, which may contain a drug, with a mixture consisting of water, a surfactant and possibly a co-surfactant pre-heated to a temperature at least equal to the melting temperature of the lipid;

b) dispersing the obtained microemulsion in water of a temperature between 2° and 10° C.;

c) washing with water through diafiltration the obtained lipid microspheres obtained in the dispersion, and lyophilizing.

As an alternative, the mixture obtained in a) is added to a mixture of water, surfactant, co-surfactant and lipids heated to a temperature at least equal to the melting temperature of said lipids, and the thus obtained mixture is dispersed in water at a temperature of 2° to 10° C.

The obtained microspheres have an average diameter smaller than one micron and in particularly of between 50 and 800 nm, preferably between 100 and 400 nm, and a polydispersion comprised between 0.06 and 0.90, preferably between 0.10 and 0.70.

DETAILED DESCRIPTION OF THE INVENTION

The characteristics and advantages of the lipid microspheres and of the process for their preparation according to the present invention will be further illustrated in the following detailed description. For the preparation of said microspheres, a lipid component or a mixture of lipid components, which may contain a pharmacologically active substance, is heated to the melting point; separately an aqueous solution containing one or more surfactants and possibly one or more co-surfactants is prepared, and the resulting solution is heated to a temperature equal at least to the melting temperature of the lipid component or mixture of lipid components; this solution is admixed under mild stirring with said lipid component or mixture of lipid components, obtaining a microemulsion; the microemulsion is poured under stirring in water of 2° to 10° C., obtaining the formation of well dispersed lipid microspheres; the dispersion is washed with water by diafiltration and finally lyophilized in the presence of suitable diluents and possibly of surface active agents which favour the re-dispersion.

Alternatively, said microemulsion is added to a mixture consisting of water, surfactant, co-surfactant and lipids, heated to a temperature at least equal to the melting temperature of said lipids and the thus obtained mixture is dispersed in water of 2° to 10° C. thus obtaining the formation of lipid microspheres.

The lipid components employed in the process of the present invention are selected in the group comprising: triglycerides, such as for instance trilaurin and tricapryloin, fatty acids such as decanoic-, lauric-, myristic-, palmitic and stearic acid; alcohols, such as lauryl-, myristyl-, cetylic-, stearyl alcohol.

The surfactants are selected from the group comprising: sodium cholate, sodium deoxycholate, sodium glycolate, sodium taurocholate, sodium taurodesoxycholate, lecithin and phospholipids, Tween 20, Tween 40, Tween 80, Span 20, Span 40, Span 60, Span 80, emulsifiers such as gelatin.

The co-surfactants are selected from the group comprising: low molecular weight alcohols or glycols, such as for instance butanol, hexanol, hexanediol, propyleneglycol, low molecular weight fatty acids, such as for instance butyric acid and hexanoic acid, esters of phosphoric acid and benzyl alcohol.

In the preparation of the microspheres according to the present invention the various substances are employed in the following proportions:

the lipid components, which may contain drugs, between 5 and 30%, preferably 10 and 20% by wt. of the total;

water, between 40 and 70%, preferably 55-65% by wt. of the total;

surfactants 8 to 30%, preferably 12-20% by wt. of the total;

co-surfactants 0-15%, preferably 3-7% by wt. of the total.

The volume of water for the dispersion of the microemulsion is from 10 to 200, and preferably from 50 to 100 volumes per volume of microemulsion.

The process according to the present invention presents, with respect to the prior art processes, numerous advantages, among which, for instance, a better control of the dimensions and of the dimensional distribution of the microspheres, a decidedly lower energy consumption and a considerably simplified operation.

Furthermore, the washing by diafiltration leads to the elimination of all the substances present in the dispersing aqueous phase (surfactant, co-surfactant and free drug not included in the microspheres).

Said compositions afford therefore an improved control on the action and effectiveness of the drug and minimize possible effects due to the simultanous undesired administration of auxiliary substances such as the surfactants.

The microspheres according to the present invention have an average diameter lower than one micron, in particularly comprised between 50 and 800 nm and preferably between 100 and 400 nm, and a polydispersion of between 0.06 and 0.90, preferably between 0.10 and 0.70, and may be successfully employed as vehicles for pharmacologically active substances and phytopharmacological substances.

To illustrate the invention the following examples are reported in which the microsphere average diameter and polydispersion were determined by means of the Malvern Zetasizer II C.

EXAMPLE 1

2 g stearic acid are melted at about 65° C. and 0.24 g deoxycorticosterone acetate are added obtaining hot a clear solution (solution 1).

Separately a solution of Tween 20 (2.5 ml), butanol (1 ml), sodium taurodeoxyglycolate (1.30 g) in 10 ml water is prepared which is brought to 65° C. (solution 2).

Solution 1 is then poured in solution 2 obtaining a clear microemulsion at 65° C., which is then dispersed under stirring in 100 volumes water per volume of microemulsion at 2° C. obtaining a lipid microsphere dispersion.

At last with water by diafiltration, mannitol is added to the dispersion, which is lyophilized.

The lipid microsphere yield on stearic acid was 96% and the deoxycorticosterone acetate contents was 4.5%.

The microspheres had an average diameter of 207 nm and the polydispersion was 0.255.

EXAMPLE 2

2 g stearic acid are heated to 65° C., while separately a mixture of 10 ml water, 1.3 g sodium taurodeoxycholate, 2.0 ml Tween 20 and 0.5 ml butyric acid is prepared and heated to 65° C.

By pouring this mixture in stearic acid under stirring a microemulsion, clear at 65° C., is obtained which is then dispersed in water (100 volumes per volume microemulsion) at 2° C. under stirring, to obtain a lipid microsphere dispersion.

After washing by diafiltration in water, the dispersion is lyophilized. The lipid microsphere yield on stearic acid was 96%. The average microsphere diameter was 142 nm and the polydispersion 0.239.

EXAMPLE 3

A mixture of 0.6 g stearic acid and 1.4 g lauric acid is heated to 47° C. Separately, a mixture of a 1% mannitol water solution, 2.75 ml Tween 20 and 1 ml butanol is heated to 47° C.

The two mixtures are put together under stirring and a microemulsion is obtained which is then dispersed at 5° C. under stirring in a 2% mannitol water solution in a ratio of 100 cc/1 cc microemulsion. After washing with water by diafiltration, lyophilization in the presence of 1% mannitol and 0.8% sodium taurodeoxycholate is performed.

The lipid microsphere yield on the lipid components was 97%. The average microsphere diameter was 250.4 nm and the polydispersion 0.591.

EXAMPLE 4

A mixture of 1.4 g palmitic acid and 0.6 g decanoic acid is heated to the melting temperature of about 50° C., while a solution of 10 ml water, 2 ml Tween 20, 1.2 g sodium taurodeoxycholate and 1 ml butanol is prepared separately and heated to 50° C.

By adding the two mixtures together, a microemulsion is obtained which is dispersed in 50 vol. water per volume of microemulsion, at 5° C. under stirring obtaining a microparticle dispersion.

Washing by diafiltration with water and lyophilization follow. The lipid microsphere yield on the lipid components was 90%, the average microsphere diameter 261 nm and the polydispersion 0.381.

EXAMPLE 5

0.4 g purified egg lecithin and 0.6 g stearic acid are admixed at 64° C., and the mixture is added to a solution of 1 ml Tween 20 in 10 ml water, apart prepared and which is heated to 64° C., under stirring.

A clear microemulsion is obtained which is dispersed in water at 2° C., in a ratio of 100 vol. water per vol. of microemulsion, under stirring.

Washing with water by diafiltration and lyophilization follow. The lipid microsphere yield on the lipid components was 87%, while the microspheres have an average diameter of 306 nm and the polydispersion is 0.667.

EXAMPLE 6

2.05 g Tween 20, 2.9 g sodium taurodeoxycholate, 1.45 g butyric acid and 15.7 g water are heated to 45° C. and to this mixture 2.5 g of a mixture of stearic and lauric acid (30:70), 0.05 g water and 0.25 g Span 60 heated to the same temperature is added.

The clear dispersion thus obtained is dispersed in 20 vol. water, obtaining microspheres with an average diameter of 350 nm, while the polydispersion is 0.56.

Washing by diafiltration and lyophilization follow. The yield is 91%.

EXAMPLE 7

0.60 g stearic acid, 0.150 g salbutamol, 0.150 g egg lecithin, mixed together at 60° C., are added to a solution containing Tween 20 (0.63 g), butyric acid (0.4), water (3 g) kept at 60° C. A clear solution is obtained which is dispersed in cold water slightly acidified with hydrochloric acid. Liposperes are obtained, which are washed by diafiltration and finally lyophilized.

Average diameter: 350 nm, polydispersion: 0.32.
Liposphere yield on the lipid components: 88%.
Salbutamol in the liposheres: 4.2%

EXAMPLE 8

To a mixture of water (7 g), taurodeoxycholate (0.9 g), butyric acid (0.65) heated to 45°–48° C., a mixture, kept at the same temperature, of (40:60) stearic and lauric acid (1.1 g), a water solution (1.4 mg/ml) of LH-RH (0.02 ml), Span 60 (0.11 g), egg lecithin (0.11 g) was added. From the obtained clear solution, by dispersion in cold water (1:25), liposheres are obtained which are washed and lyophilized. Liposhere yield (on the lipid components): 85%.

LH-RH in the liposheres: 0.015%.
Average diameter: 360 nm, polydispersion: 0.42.

EXAMPLE 9

1.2 g stearic acid are added, at 60° C., to 0.160 g estradiol and 0.300 g egg lecithin, then the whole is admixed with a butanol (0.5 g) solution in 7 g water and Tween 20 (0.75 g). A clear solution is obtained which is dispersed in cold water. Liposheres are obtained which are then washed by diafiltration and lyophilized.

Liposhere yield (on the lipid components): 75%.
Average liposhere diameter: 310 nm, polydispersion: 0.20.
Estradiol in the liposheres: 5.2%.

EXAMPLE 10

2 g stearic acid, 0.5 g naphtalene-acetic acid are admixed at 60° C. and added to a mixture, kept at 60° C., of butyric acid (0.6 g), taurodeoxycholate (1.3 g), Tween 20 (2 g), water (10 g). A clear solution is obtained which is then dispersed in cold water.

After washing by diafiltration and lyophilization, liposheres of an average diameter of 420 nm and 0.32 polydispersion are obtained.

Yield on the lipid components: 85%. Naphtalene-acetic acid in the liposheres: 4.1%.

EXAMPLE 11

A mixture consisting of 0.031 ml of a water solution (5 mg/ml) of salmon calcitonin, 1.38 g stearic acid, 0.148 g Span 40 is prepared at 65°–70° C. This mixture is added to another mixture consisting of 6.85 g water, 0.84 g taurodeoxycholate, 0.59 g butanol and 8.16 g Tween 20, and kept at 65°–70° C. The clear solution obtained is dispersed in cold water (1:25) and the liposheres are washed and lyophilized. Liposhere yield, on the lipid components: 90%.

Average diameter: 300 nm, polydispersion: 0.5.
Calcitonin in the liposheres: 0.5%.

EXAMPLE 12

A mixture consisting of 0.032 ml of a water solution (2 mg/ml) somatostatin, 1.61 g palmitic/stearic acid (50:50) and 0.157 g Span 80, is prepared at 60°–65° C.; this mixture is then added, always at 60°–65° C., to another mixture prepared with 9.675 g water, 0.75 g taurodeoxycholate, 0.57 g butyric acid, 2.13 g Tween 80, 0.075 g lecithin. The clear solution obtained is dispersed in cold water and the liposheres are washed by diafiltration and lyophilized.

Liposhere yield, on the lipids: 88%.

Average diameter: 310 nm, polydispersion: 0.40.
Somatostathin in the liposheres: 0.15%.

EXAMPLE 13

A mixture consisting of 0.022 ml of a water solution (5 mg/ml) of erythropoietin, 1.0 g stearic/myristic acid (50:50) and 9.0 g Span 60 is prepared at 55°–60° C.; this mixture is then added, always at 55°–60° C., to another mixture prepared from 5.535 g water, 0.495 g taurodeoxycholate, 1.35 g sodium laurylsulphate, 0.495 g butanol. The clear solution obtained is dispersed in cold water; the lipid nanospheres obtained are washed and then lyophilized, with a yield of 83% on the lipids.

Erythropoietin in the liposheres: 0.4%.
Average diameter: 390 nm, polydispersion: 0.35.

I claim:

1. Process for preparing solid lipid microspheres with an average diameter below 1 micron and a polydispersion of between 0.06 and 0.90 and preferably between 0.10 and 0.70, wherein:
   a) a molten lipid, which may contain a drug, is contacted with a mixture consisting of water, a surfactant and possibly a co-surfactant heated to a temperature at least equal to the melting temperature of the lipid;
   b) the obtained microemulsion is dispersed in water of 2° to 10° C.;
   c) the obtained lipid microsphere dispersion is washed with water by diafiltration and lyophilized.

2. Process according to claim 1, wherein the microemulsion obtained in a) is added to a mixture consisting of water, surfactant, co-surfactant and lipids heated to a temperature at least equal to the melting temperature of said lipid substances and the thus obtained mixture is dispersed in water of 2° to 10° C.

3. Process according to claim 1, wherein said lipid substance consists of one or more components selected from the group consisting of trilaurin, tricapryloin, decanoic acid, lauric acid, myristic acid, palmitic acid, stearic acid, lauryl alcohol, myristyl alcohol, cetyl alcohol and stearyl alcohol.

4. Process according to claim 1, wherein said surfactant comprises one or more components selected from the group consisting of sodium cholate, sodium deoxycholate, sodium glycocholate, sodium taurocholate, sodium taurodeoxycholate, lecithin, Tween 20, Tween 40, Tween 80, Span 20, Span 40, Span 60, Span 80 and gelatin.

5. Process according to claim 1, wherein said co-surfactant comprises one or more components selected from the group consisting of butanol, hexanediol, propyleneglycol, hexanol, butyric- and hexanoic acid, phosphoric acid esters and benzyl alcohol.

6. Process according to claim 1, wherein in step a) the lipid comprises between 5 and 30%, water between 40 and 70%, the surfactant between 8 and 30% and the co-surfactant between 0 and 15% by wt. of the total.

7. Process according to claim 1, wherein in stage a) the lipid comprises between 10 and 20%, the water between 12 and 20% and the co-surfactant between 3 and 7% by weight of the total.

8. The process according to claim 1, wherein in stage b) the quantity of water employed is of between 10 and 200 volumes per volume of said microemulsion.

* * * * *